US009078724B2

(12) United States Patent
Devins

(10) Patent No.: US 9,078,724 B2
(45) Date of Patent: Jul. 14, 2015

(54) DENTAL FLOSS APPARATUS

(71) Applicant: Jeremy Angelo Devins, Simi Valley, CA (US)

(72) Inventor: Jeremy Angelo Devins, Simi Valley, CA (US)

( * ) Notice: Subject to any disclaimer, the term of this patent is extended or adjusted under 35 U.S.C. 154(b) by 0 days.

(21) Appl. No.: 14/323,435

(22) Filed: Jul. 3, 2014

(65) Prior Publication Data

US 2015/0007844 A1 Jan. 8, 2015

Related U.S. Application Data

(60) Provisional application No. 61/843,780, filed on Jul. 8, 2013.

(51) Int. Cl.
*A61C 15/00* (2006.01)
*A61C 15/04* (2006.01)

(52) U.S. Cl.
CPC .................... *A61C 15/046* (2013.01)

(58) Field of Classification Search
CPC ........ A61C 15/00; A61C 15/02; A61C 15/04; A61C 15/1043; A61C 15/045; A61C 15/046; A61C 19/02; A61C 19/063; A61C 8/0087; A61Q 11/00
USPC ......... 132/324, 200, 309, 321, 323, 325–329; 206/581, 823, 63.5
See application file for complete search history.

(56) References Cited

U.S. PATENT DOCUMENTS

| 1,239,633 | A | * | 9/1917 | Stickler | 132/324 |
| 1,480,101 | A | * | 1/1924 | Ogden | 132/324 |
| 1,815,408 | A | * | 7/1931 | Jordan | 132/323 |
| 1,990,404 | A | * | 2/1935 | Doner | 132/326 |
| 2,354,454 | A | * | 7/1944 | Geffner | 132/323 |
| 2,376,750 | A | * | 5/1945 | Bell | 132/324 |
| 2,756,758 | A | * | 7/1956 | Segerblom | 132/326 |
| 2,784,722 | A | * | 3/1957 | Chamberlin et al. | 132/324 |
| 2,853,082 | A | * | 9/1958 | Nelson | 132/326 |
| 2,870,773 | A | * | 1/1959 | Parks, Jr. | 132/326 |
| 3,094,996 | A | * | 6/1963 | Lewis | 132/324 |
| 3,376,876 | A | * | 4/1968 | Wicklund | 132/324 |
| 3,913,597 | A | * | 10/1975 | Day | 132/324 |
| 3,949,769 | A | * | 4/1976 | Minka | 132/324 |
| 4,052,994 | A | * | 10/1977 | Thun | 132/325 |
| 4,206,774 | A | * | 6/1980 | Griparis | 132/326 |
| 4,326,548 | A | * | 4/1982 | Wagner | 132/328 |
| 4,574,823 | A | * | 3/1986 | Uriss | 132/325 |
| 4,800,905 | A | * | 1/1989 | Stuart | 132/328 |
| 5,078,526 | A | * | 1/1992 | Corona | 401/125 |
| 5,141,008 | A | * | 8/1992 | Lee | 132/325 |
| 5,503,169 | A | * | 4/1996 | Won | 132/325 |
| 5,573,021 | A | * | 11/1996 | Grofcisk et al. | 132/324 |
| 2005/0247328 | A1 | * | 11/2005 | Shen et al. | 132/325 |
| 2008/0163888 | A1 | * | 7/2008 | Chen | 132/323 |
| 2014/0144461 | A1 | * | 5/2014 | Chiang | 132/323 |
| 2014/0335474 | A1 | * | 11/2014 | Shaw | 433/216 |

* cited by examiner

*Primary Examiner* — Vanitha Elgart
(74) *Attorney, Agent, or Firm* — Kelly & Kelley, LLP

(57) ABSTRACT

A compact and reusable floss pick having a dispensing supply of dental floss. A floss arm and bridge is provided with two prongs for receiving a length of dental floss removably wrapped around the prongs such that a taut length of dental floss is provided therebetween. A cutting notch is provided for removing an old or used portion of dental floss from the supply. A removable cap is also provided for covering the floss arm when not in use and providing a handle when the device is being used.

15 Claims, 7 Drawing Sheets

DENTAL FLOSS APPARATUS

RELATED APPLICATION

This application claims the benefit of U.S. Provisional Application No. 61/843,780, filed on Jul. 8, 2013.

BACKGROUND OF THE INVENTION

The present invention is directed to a device for facilitating the carrying and use of dental floss. More particularly, the present invention is directed to a compact and mobile device including a supply of dental floss and an extended arm having a bridge with two prongs for removably attaching a length of dental floss.

Dental floss is widely accepted as an appropriate means to clean between and around one's teeth, particularly after a meal. However, dental floss on its own can be difficult and cumbersome to use as one is usually required to wrap the floss around one's fingers and place them inside their mouth. In the privacy of one's own home or bathroom, such may be acceptable. Out in public, as in a restaurant setting, it would not be as acceptable.

Disposable floss picks comprising an instrument having two prongs extending from a body with a single piece of floss running between the prongs are available. In such devices the dental floss is previously and permanently attached to the prongs such that the instrument is often single-use and disposed of after such use. In order to have such an instrument for every meal, one must either carry around a supply of the instruments or remember to replace each one after each meal.

Accordingly, there is a need for a device to facilitate the use of dental floss while on the go and in a manner that is convenient and reusable. The present invention fulfills these needs and provides other related advantages.

SUMMARY OF THE INVENTION

The present invention is directed to a dental floss apparatus, in particular a reuseable dental floss tool having a renewable and replaceable supply of dental floss. The apparatus consists of a floss arm having a floss bridge at a distal end and a hollow base at a proximal end. A pair of prongs is included on the floss bridge defining a gap between the pair of prongs. The floss arm and floss bridge are preferably configured in an "F"-shape or a "Y"-shape.

Each of the pair of prongs includes a notched portion adjacent to a free end of the prong. A supply of dental floss is contained within the hollow base, with the hollow base having a dispensing hole proximate to the floss arm. The supply of dental floss is removable and replaceable. A loose end of the supply of dental floss is passable through the dispensing hole and wrappable around the notched portion on each of the pair of prongs. When wrapped around the notched portion on each of the pair of prongs, the dental floss forms a taut length of dental floss between the first and second prongs.

The notched portion of at least one of the pair of prongs preferably includes a textured or adhesive surface configured to securely retain the dental floss wrapped there around. Ideally, both notched portions include the textured or adhesive surface. Furthermore, the notched portion of each of the pair of prongs is configured to have a straight-V cross-section or an angled-V cross-section. An elongated cap is configured to cover the floss arm and floss bridge when not in use and then be removed and stored on a bottom of the hollow base when the floss arm and floss bridge are being used.

A floss blade for cutting the dental floss is preferably disposed on the floss arm proximate to the floss bridge. A floss pick is preferably disposed on one of the pair of prongs of the floss bridge. Preferably, the floss arm and floss bridge are made from surgical grade metal or surgical grade plastic, both of which are configured to hinder bacterial and microbial growth.

A method for using the dental floss apparatus includes providing a dental floss apparatus having a hollow base containing a supply of dental floss, a floss arm extending from the hollow base and a floss bridge on a distal end of the floss arm. A loose end of the supply of dental floss is pulled through a dispensing hole in the hollow base. A first portion of the loose end of the supply of dental floss is wrapped around a first prong on the floss bridge, and a second portion of the loose end of the supply of dental floss is wrapped around a second prong on the floss bridge. A taut length of dental floss is thus formed spanning between first prong and the second prong.

The method may further include the steps of unwrapping the loose end of the supply of dental floss from the second prong and the first prong. The unwrapped loose end of the dental floss is then cut using a floss blade disposed proximate to the floss bridge. The supply of dental floss may be removed from the hollow base, and a replacement supply of dental floss may then be inserted into the hollow base.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
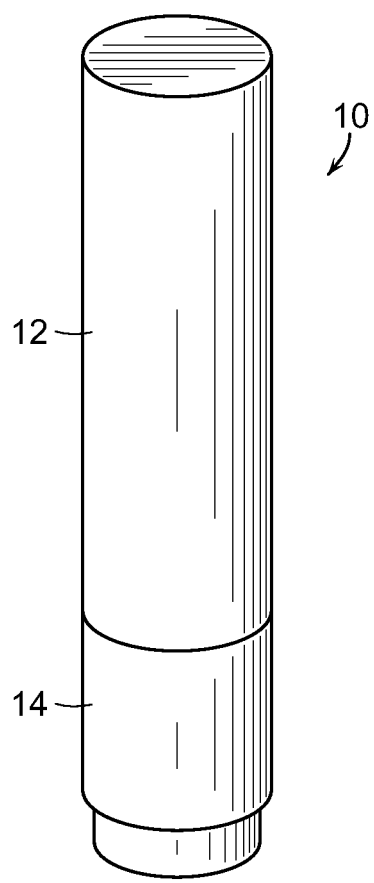
FIG. 1 is a perspective view of the device of the present invention.
Figure 2:
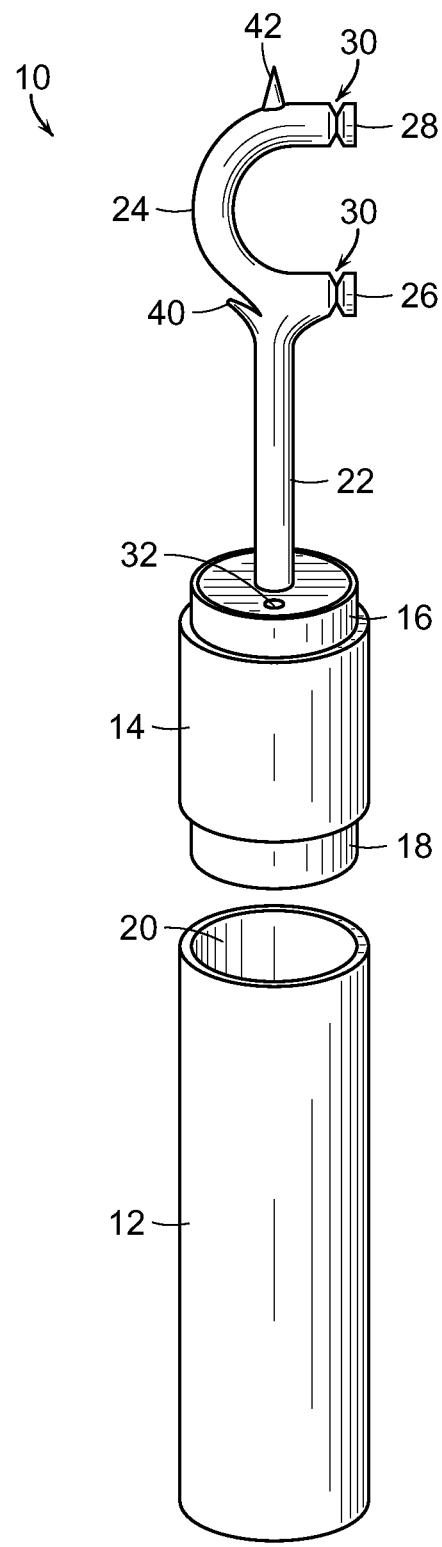
FIG. 2 is a perspective view of the device with the cap removed.
Figure 3:
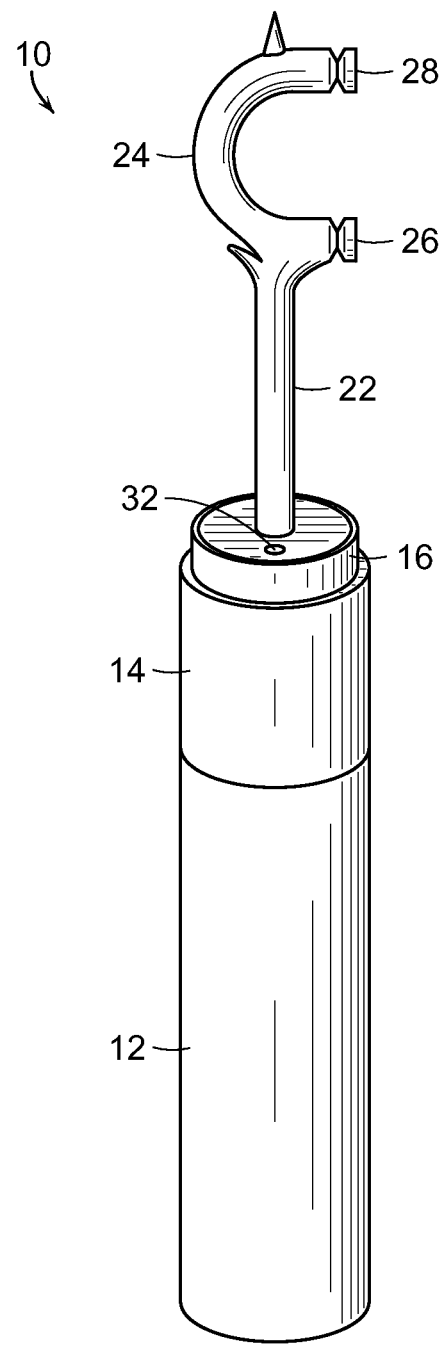
FIG. 3 is a perspective view of the device with the cap attached to the base.
Figure 4:
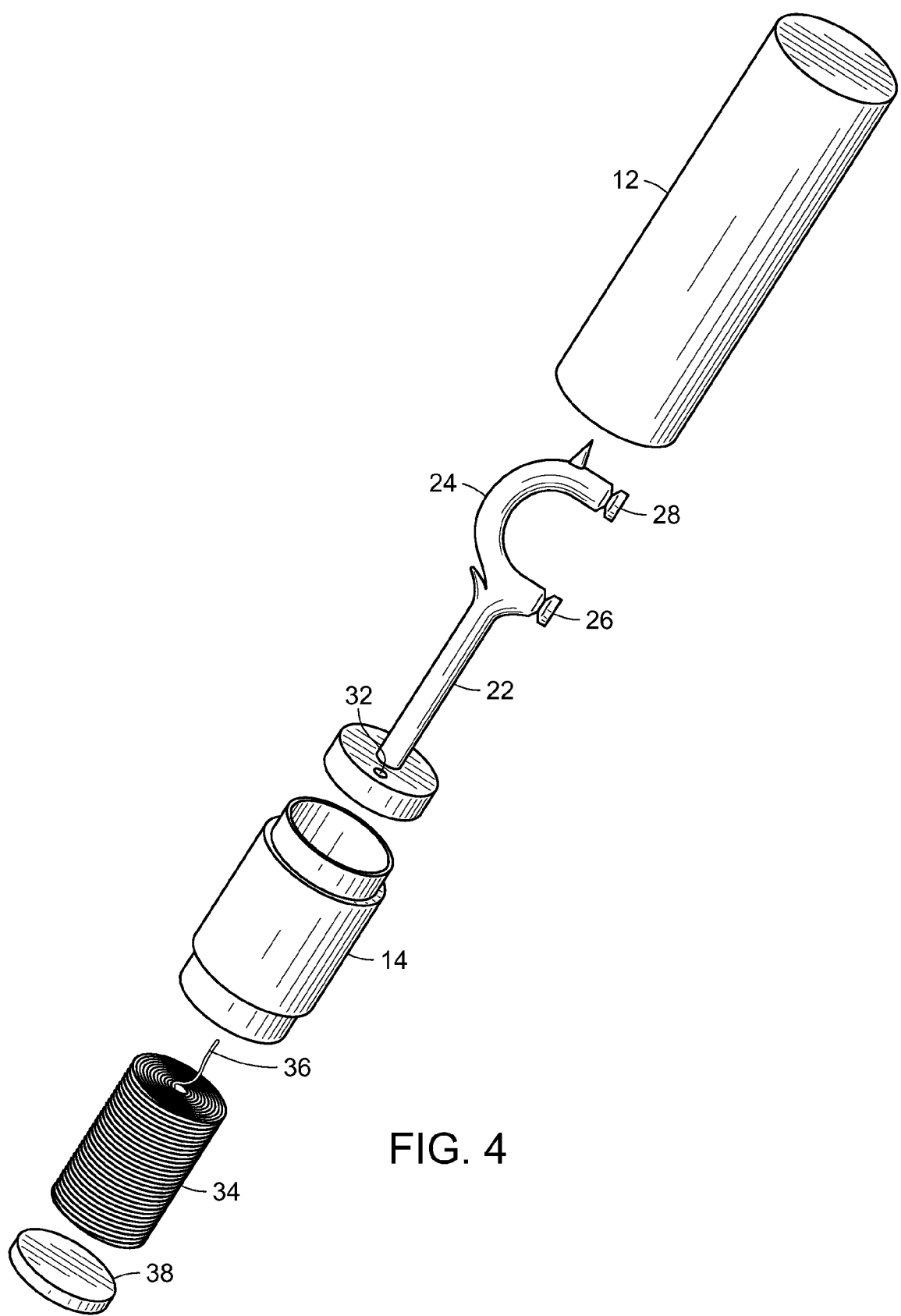
FIG. 4 is an exploded view of the device.

The present invention is directed to a reusable dental floss pick generally referred to by reference numeral 10 in FIGS. 1-7. The floss pick 10 includes a cap 12 and base 14. The cap 12 is removable from the base 14. The base 14 preferably includes an upper protrusion 16 and a lower protrusion 18, both of which are configured to accept an opening 20 on the cap 12. The relative diameters of the upper and lower protrusions 16,18 and the opening 20 are such that a snug or friction fit occurs when they are brought together. In this way, the cap 12 can be retained on the upper protrusion 16 to protect the pick 10 when not in use and on the lower protrusion 18 to provide additional support for gripping the device 10 when being used.

A floss arm 22 extends from the upper protrusion 16. The floss arm 22 has a bridge portion 24 at a distal end. The bridge portion 24 has a first prong 26 and a second prong 28. The floss arm 22, bridge portion 24, first prong 26, and second prong 28 may be constructed using a cylindrical configuration such that each portion has a generally rounded cross-section. Alternatively, these portions may be constructed using a flattened configuration such that each portion has a generally oval or oblong cross-section.

Figure 5:
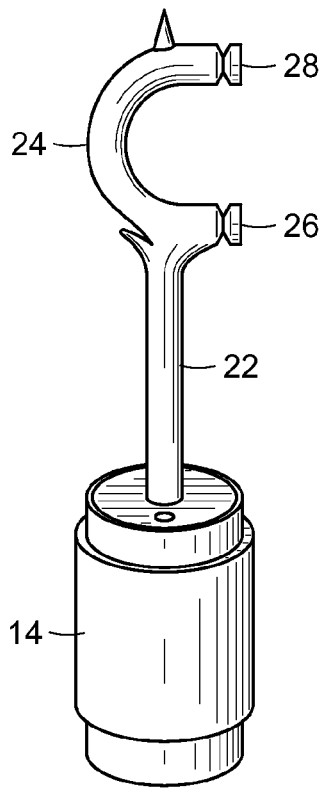
FIG. 5 is a detailed view of the device without the cap.
Figure 5A:
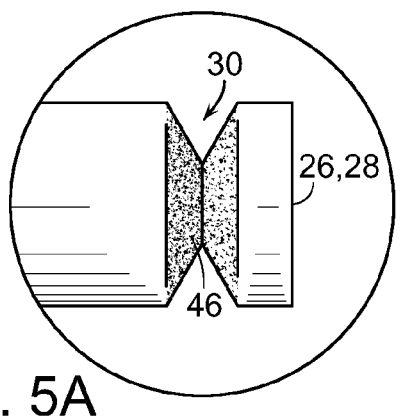
FIG. 5A is a close-up view of the prongs on the bridge.
Figure 5B:
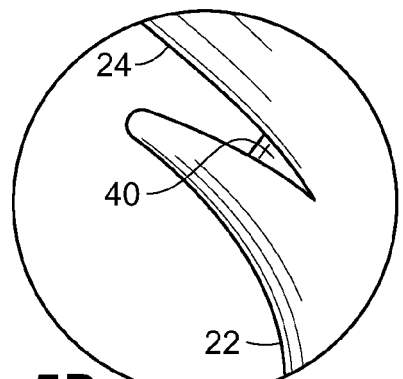
FIG. 5B is a close-up view of a cutting notch.
Figure 5C:
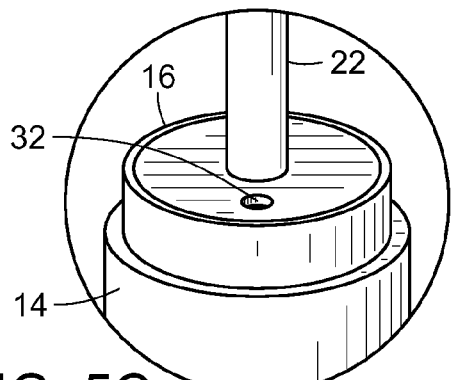
FIG. 5C is a close-up view of a dispensing hole.
Figure 5E:
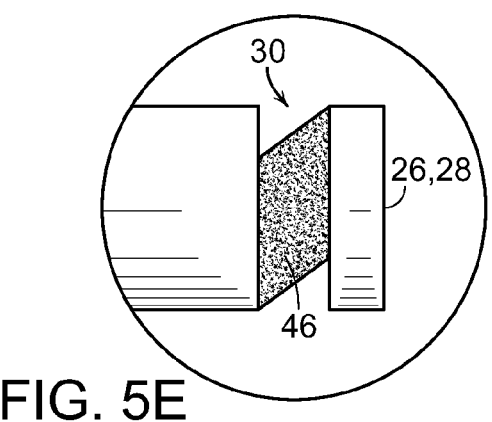
FIG. 5E is a close-up view of an alternate embodiment of the prongs on the bridge.

As more clearly illustrated in FIGS. 5A and 5E, each prong 26, 28 includes a notched portion 30 proximate to the end of the prong 26, 28. In FIG. 5A, the notched portion 30 generally has a straight-"V" shape or cross-section. The notched portion 30 may comprise opposite mirror "V" shaped notches when used on a flattened prong 26, 28 or an annular "V" shape configuration when used on a cylindrical prong 26, 28. As shown in FIG. 5E, the notched portion 30 may have a sloped or angled-"V" shape or cross-section configured as described for either a flattened or cylindrical prong 26, 28. The notched portion 30 may be included on both prongs 26, 28 or only one of the prongs 26, 28, i.e., the prong 26, 28 that receives the last winding of the dental floss. As clearly shown in FIG. 5C, a dispensing hole 32 is disposed in the top of the upper protrusion 16 adjacent to where a proximate end of the floss arm 22 is attached to the upper protrusion 16.

Figure 5D:
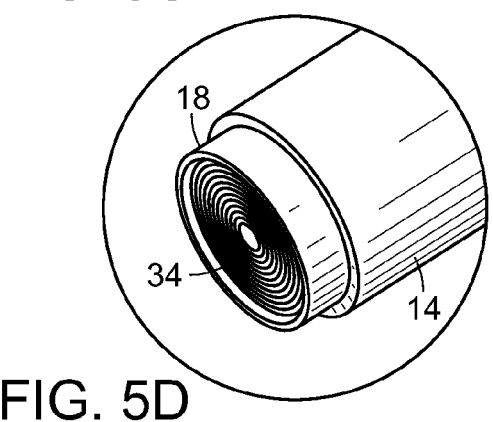
FIG. 5D is a close-up view of the dental floss inserted in the base.
Figure 6:
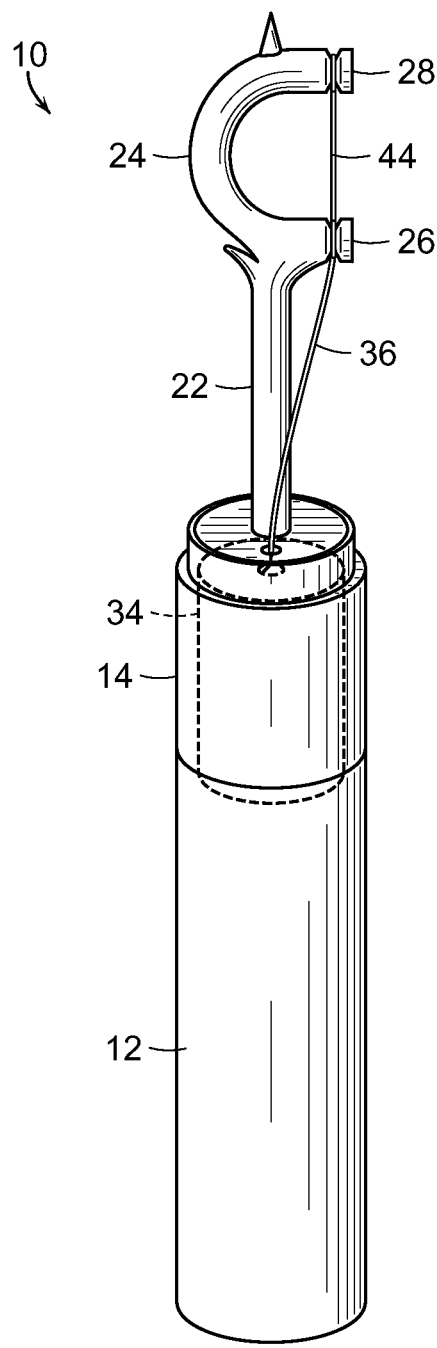
FIG. 6 is a partial cutaway of the device illustrating the dental floss dispensed and attached to the prongs of the bridge.

The base 14 is hollow and configured to contain therein a supply of dental floss 34 as shown in FIG. 5D. The supply of dental floss 34 may be provided in a wound cylinder, cartridge, or similar format such that the dental floss 34 will freely unwind when a loose end 36 is pulled. The dental floss 34 may be in any form commonly used in such dental instruments and may be coated in wax, fluoride, flavored compounds, or other similar materials. A lid 38 encloses the bottom of the base 14 to seal the dental floss 34 therein. The lid 38 is preferably transparent or translucent in design so that one may easily observe the remaining quantity of dental floss 34 contained in the base 14.

The floss arm 22 preferably includes a floss blade or cutting notch 40 disposed proximate to the bridge 24 as shown in FIG. 5B. The cutting notch 40 is configured to provide a sharp edge, whether plastic or metal, on which to cut the dental floss 34. In addition, a toothpick 42 may be included in a distal end of the bridge 24 or in a similar position that does not interfere with use of the pick 10.

In use, the loose end 36 of the dental floss 34 is passed through the dispensing hole 32. A sufficient length of dental floss 34 is pulled through the hole 32 and one winds a portion thereof around the notch portion 30 of the first prong 26. With sufficient additional length, one then pulls the dental floss 34 taut and winds another portion around the notched portion 30 of the second prong 28. In this way, a taut length 44 of dental floss 34 spans the distance between the prongs 26, 28. This taut length 44 of dental floss 34 can then be used to floss between a person's teeth, similar to the way in which prior art disposable floss picks are used.

With the device 10 a person does not need to place their fingers inside their mouth to hold both ends of a length of dental floss. In addition, the inventive pick 10 is not disposable or single-use as the taut length 44 of dental floss 34 can be removed and replaced after each use. After flossing one's teeth, one may then unwind the dental floss 34 from the prongs 26, 28 and cut the used portion of dental floss 34 using the cutting notch 40.

The notched portions 30 on the prongs 26, 28 preferably have a textured or adhesive surface 46. This surface 46 provides a better grip and retention of the dental floss 34 around the notched portion 30. The cutting notch 40, also referred to as a floss blade, can be used to cut the dental floss 34 either before use to provide a fresh length of dental floss 34 or after use to remove a portion of the dental floss 34 that has been used. The toothpick 42 may also be used to pick between a person's teeth to remove larger bits of food.

All of the parts of the device 10 are preferably manufactured from surgical grade metal, plastic or similar material commonly used in such dental appliances. Preferably, the material is of such construction that the growth of bacteria and similar microbes is not promoted or even hindered. An antibacterial compound may be impregnated within the material or coat the outside. As explained above, the floss blade or cutting notch 40 may include a plastic or metal cutting edge.

Figure 7:
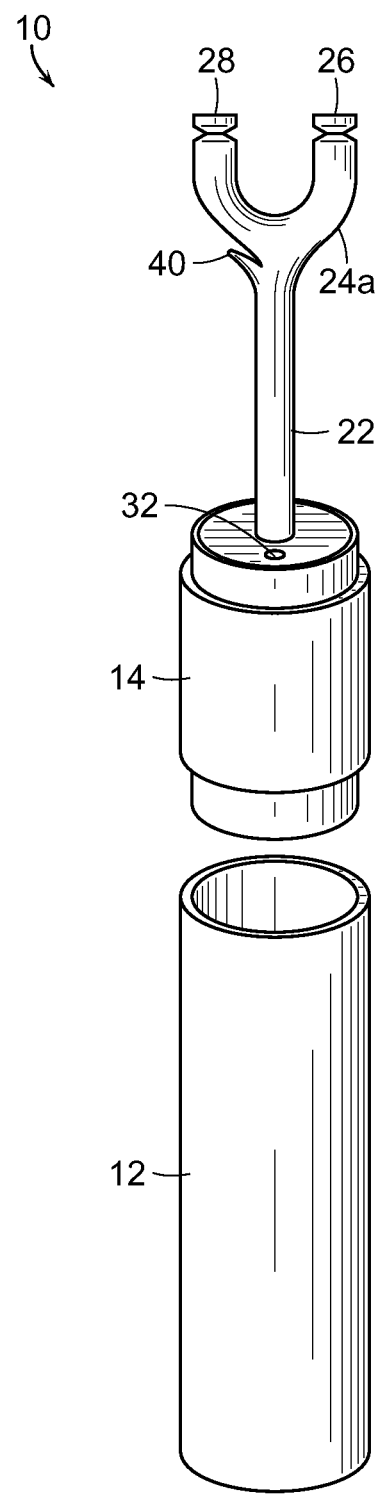
FIG. 7 is a perspective view of an alternate embodiment of the device.

The bridge 24 may be presented in either an "F" shape as illustrated in FIGS. 1-6 or a "Y" shape as illustrated in FIG. 7. The device 10 having the "Y"-shaped bridge 24a has utility and function in the same manner as described above.

Although several embodiments have been described in detail for purposes of illustration, various modifications may be made without departing from the scope and spirit of the invention. Accordingly, the invention is not to be limited, except as by the appended claims.

What is claimed is:

1. A dental floss apparatus, comprising:
  a floss arm having a floss bridge at a distal end and a hollow base at a proximal end;
  a pair of prongs included on the floss bridge defining a gap between the pair of prongs, wherein each of the pair of prongs includes a notched portion having an angled-V cross-section adjacent to a free end of the prong; and
  a supply of dental floss contained within the hollow base and the hollow base having a dispensing hole proximate to the floss arm, wherein a loose end of the supply of dental floss is passable through the dispensing hole and wrappable around the notched portion on each of the pair of prongs so as to form a taut length of dental floss between the pair of prongs.

2. The dental floss apparatus of claim 1, wherein the notched portion of at least one of the pair of prongs includes a textured or adhesive surface configured to securely retain the dental floss wrapped there around.

3. The dental floss apparatus of claim 1, further comprising a removable elongated cap configured to cover the floss arm and floss bridge when not in use and be stored on a bottom of the hollow base when the floss arm and floss bridge are being used.

4. The dental floss apparatus of claim 1, further comprising a floss blade disposed on the floss arm proximate to the floss bridge.

5. The dental floss apparatus of claim 1, further comprising a toothpick disposed on one of the pair of prongs of the floss bridge.

6. The dental floss apparatus of claim 1, wherein the floss arm and floss bridge are made from surgical grade metal or surgical grade plastic, both configured to hinder bacterial and microbial growth.

7. The dental floss apparatus of claim 1, wherein the floss arm and floss bridge are configured in an "F"-shape or a "Y"-shape.

8. The dental floss apparatus of claim 1, wherein the supply of dental floss is removable and replaceable.

9. A dental floss apparatus, comprising:

a floss arm having a floss bridge at a distal end and a hollow base at a proximal end, wherein the floss arm and floss bridge are made from surgical grade metal or plastic, coated or impregnated with an antibacterial compound configured to hinder bacterial and microbial growth;

a pair of prongs included on the floss bridge defining a gap between the pair of prongs, wherein each of the pair of prongs includes a notched portion adjacent to a free end of the prong, wherein the notched portion of at least one of the pair of prongs includes a textured or adhesive surface;

a supply of dental floss contained within the hollow base and the hollow base having a dispensing hole proximate to the floss arm, wherein a loose end of the supply of dental floss is passable through the dispensing hole and wrappable around the notched portion on each of the pair of prongs such that the textured or adhesive portion on at least one of the pair of prongs securely retains the dental floss wrapped there around so as to form a taut length of dental floss between the pair of prongs; and a removable elongated cap configured to cover the floss arm and floss bridge when not in use and be stored on a bottom of the hollow base when the floss arm and floss bridge are being used.

10. The dental floss apparatus of claim 9, wherein the notched portion of each of the pair of prongs is configured to have a straight-V cross-section or an angled-V cross-section.

11. The dental floss apparatus of claim 9, further comprising a floss blade disposed on the floss arm proximate to the floss bridge.

12. The dental floss apparatus of claim 9, further comprising a toothpick disposed on one of the pair of prongs of the floss bridge.

13. The dental floss apparatus of claim 9, wherein the floss arm and floss bridge are configured in an "F"-shape or a "Y"-shape.

14. The dental floss apparatus of claim 9, wherein the supply of dental floss is removable and replaceable.

15. A dental floss apparatus, comprising:

a floss arm having a floss bridge at a distal end, a hollow base at a proximal end, and a floss blade proximate to the floss bridge, wherein the floss arm and floss bridge are made from surgical grade metal or plastic, coated or impregnated with an antibacterial compound configured to hinder bacterial and microbial growth, and wherein the floss arm and floss bridge are configured in an "F"-shape or a "Y"-shape;

a pair of prongs included on the floss bridge defining a gap between the pair of prongs, wherein each of the pair of prongs includes a notched portion having a straight-V or an angled-V cross-section adjacent to a free end of the prong, wherein the notched portion of at least one of the pair of prongs includes a textured or adhesive surface;

a toothpick disposed on one of the pair of prongs;

a removable and replaceable supply of dental floss contained within the hollow base and the hollow base having a dispensing hole proximate to the floss arm, wherein a loose end of the supply of dental floss is passable through the dispensing hole and wrappable around the notched portion on each of the pair of prongs such that the textured or adhesive portion on at least one of the pair of prongs securely retains the dental floss wrapped there around so as to form a taut length of dental floss between the pair of prongs; and a removable elongated cap configured to cover the floss arm and floss bridge when not in use and be stored on a bottom of the hollow base when the floss arm and floss bridge are being used.

\* \* \* \* \*